(12) United States Patent
Diehl

(10) Patent No.: US 6,712,945 B2
(45) Date of Patent: Mar. 30, 2004

(54) ELECTROCHEMICAL SENSOR

(75) Inventor: Lothar Diehl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 65 days.

(21) Appl. No.: 09/840,523

(22) Filed: Apr. 23, 2001

(65) Prior Publication Data

US 2002/0017462 A1 Feb. 14, 2002

(30) Foreign Application Priority Data

Apr. 22, 2000 (DE) .......................................... 100 20 082

(51) Int. Cl.$^7$ ............................................. G01N 27/407
(52) U.S. Cl. ....................... 204/424; 204/421; 204/426; 204/427
(58) Field of Search ................................. 204/421–429

(56) References Cited

U.S. PATENT DOCUMENTS

| | | | | |
|---|---|---|---|---|
| 3,598,711 A | * | 8/1971 | Flais | |
| 3,843,400 A | * | 10/1974 | Radford et al. | |
| 4,289,802 A | * | 9/1981 | Micheli | |
| 4,668,375 A | * | 5/1987 | Kato et al. | |
| 4,720,335 A | * | 1/1988 | Fukushima et al. | |
| 5,393,397 A | * | 2/1995 | Fukaya et al. | |
| 5,486,279 A | * | 1/1996 | Friese et al. | |
| 5,716,507 A | * | 2/1998 | Tanaka et al. | |
| 6,436,277 B2 | * | 8/2002 | Schnaibel et al. | |

OTHER PUBLICATIONS

Wiedenmann et al., "Exhaust Gas Sensors", *Automotive Electronics Handbook* (1994), Chapter 6.

* cited by examiner

*Primary Examiner*—T. Tung
(74) *Attorney, Agent, or Firm*—Kenyon & Kenyon

(57) ABSTRACT

An electrochemical sensor for determining gas components and/or gas concentrations in gas mixtures using a sensor element is described; it has at least one electrode arranged on an ion-conducting solid electrolyte body bordering on a gas space in at least some areas. The electrode has at least two layers, the second layer which faces the gas space having a higher electron conductivity in comparison with the first layer which faces the solid electrolyte body.

20 Claims, 1 Drawing Sheet

ELECTROCHEMICAL SENSOR

FIELD OF THE INVENTION

The present invention relates to an electrochemical sensor.

BACKGROUND INFORMATION

Electrochemical sensors for use in analyzing exhaust emissions from internal combustion engines are described in, for example, from chapter 6 "Exhaust Gas Sensors" in *Automotive Electronics Handbook* (1994), by Wiedenmann et al. Such sensors contain a sensor element having at least one electrode with an electrode lead arranged on a first ion-conducting solid electrolyte body and bordering at least some areas of a gas space provided in a second solid electrolyte body. The electrode is made of a cermet material in which the ceramic component is composed of, for example, 40 vol % $ZrO_2$ stabilized with $Y_2O_3$ and the metallic component is platinum.

Such an electrode permits the exchange of oxygen between the gas space and the first solid electrolyte body, where the oxygen molecule $O_2$ goes from the gas phase, takes up $4e^-$ from the metallic component of the electrode, and converts it into two oxygen ions $2O^{2-}$ in the ceramic component of the electrode. The oxygen exchange thus takes place at the ternary or three-phase boundaries of the electrode, i.e., those areas of the electrode where the ceramic component, the metallic component and the gas space share a common boundary. Oxygen ions pass over the ceramic component of the electrode into the first solid electrolyte body, and electrons flow over the metallic component of the electrode and the electrode lead to a circuit outside the sensor element. The electrode has a certain porosity due to the addition of $Y_2O_3$ to the $ZrO_2$, thus forming ternary boundaries not only on the outer surface of the electrode facing the gas space but also inside the electrode.

Because of its high ceramic content, electron conduction by the electrodes is impaired. If the platinum content of the electrode is increased relative to the content of ceramic component in order to increase electron conductivity, this results in an impairment in ionic conductivity and a reduction in porosity.

In determining the lambda value of an exhaust gas, it is also important for the exhaust gas to be in thermodynamic equilibrium in the area of the ternary boundaries. For this, the exhaust gas is converted by way of a catalyst to a state sufficiently approximating a thermodynamic equilibrium. The catalytic effect is achieved by catalytically active platinum. Under unfavorable conditions, however, the catalytic effect of platinum with such electrodes is inadequate for establishing the thermodynamic equilibrium.

Furthermore, German Patent No. 29905601.5 describes a design for an electrode wherein the electrode extends at least laterally beyond the gas space and into the area between the first and second solid electrolyte bodies. Therefore, the tensile stress that occurs because of local temperature differences when the sensor element is heated by a heating element is reduced by the good thermal conductivity of the electrode. However, one disadvantage of this electrode design is that the electrode has a low internal resistance with respect to ionic conduction because of its $ZrO_2$ content, so that mixed potentials may occur and interfere with proper functioning of the sensor element.

SUMMARY OF THE INVENTION

The electrochemical sensor according to the present invention has the advantage in comparison with the related art that electron conduction in the electrode is improved. The current occurring with the oxygen exchange forms the measurement signal and flows mainly over the second layer due to the fact that the electrode has at least two layers—a second layer which faces the gas space and conducts electrons better than a first layer which faces the first solid electrolyte body. Therefore, in the case of a pump electrode, for example, the pump function is improved because of the reduced drop in pump voltage across the pump electrode applied by an external circuit.

Due to the porous design of the second layer, the gas to be analyzed can pass from the gas space through the second layer and can reach the first layer of the electrode. Adding a pore-forming agent according to the present invention to the second layer of the electrode makes it furthermore possible for the exhaust gas to pass from the gas space to the first layer, overcoming just a low diffusion resistance. At the same time, the amount of pore-forming agent used is so low that the electron conductivity of the second layer is not impaired by an excessively high porosity.

Due to the use of platinum as the metallic component of the second layer of the electrode in particular, the gas can achieve a thermodynamic equilibrium more reliably in passing through the second layer. The second layer can be stabilized mechanically by adding $Al_2O_3$. Furthermore, ionic conductivity is advantageously improved by adding $Yb_2O_3$ and/or $In_2O_3$ to the first layer of the electrode, and electron conductivity is improved by adding $TiO_2$ to the first layer of the electrode.

The electrode lead also has good electron conductivity due to the fact that at least one layer made of the same material as the second layer of the electrode is provided for an electrode lead to the electrode.

Mixed potentials which cause problems with respect to ionic conduction because of the high resistance of the second layer are largely prevented because the second layer of the electrode is designed to be wider than the gas space at least across the longitudinal extent of the sensor element, so that the second layer extends into the area between the first and second solid electrolyte bodies.

DETAILED DESCRIPTION

Figure 1:
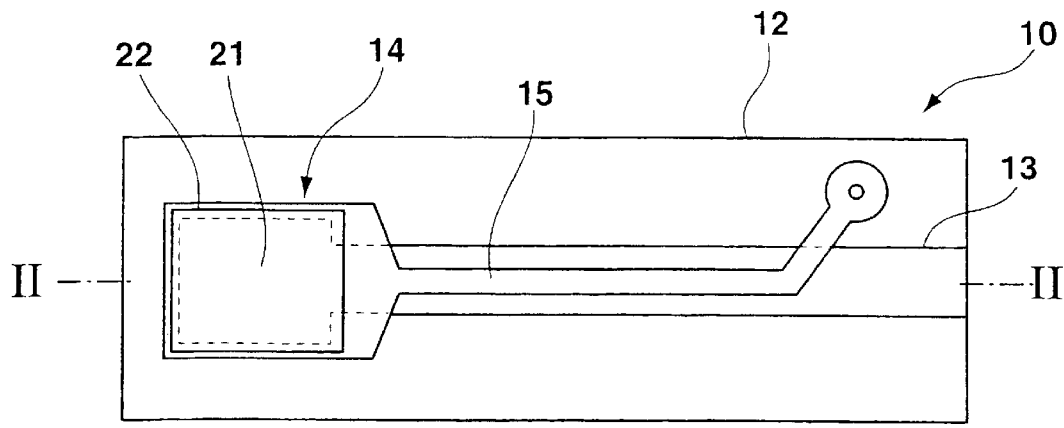
FIG. 1 shows a top view of a large area of a sensor element according to a first embodiment of the present invention.
Figure 2:
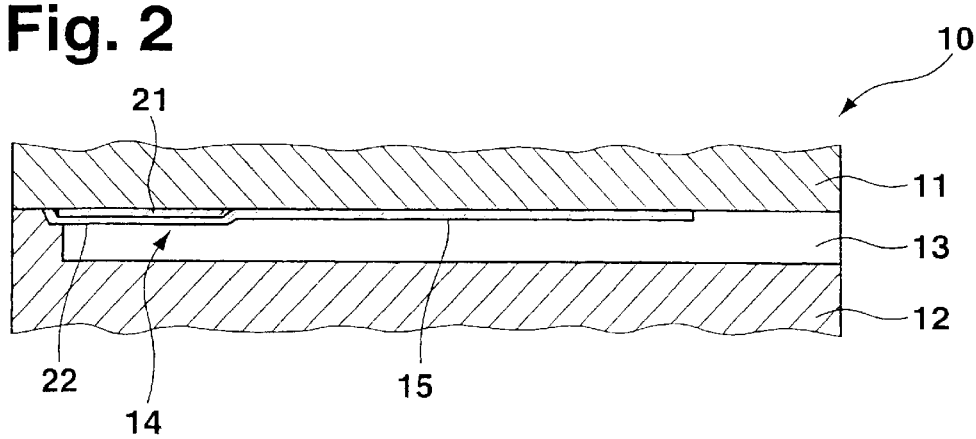
FIG. 2 shows a sectional diagram of the sensor element along line II—II in FIG. 1.

FIGS. 1 and 2 illustrate as the first embodiment of the present invention a detail of a sensor element 10 having a first and a second solid electrolyte body 11, 12; FIG. 2 shows a side view, omitting the first solid electrolyte body 11. A gas space 13 connected to a reference space or an exhaust gas space outside the sensor element, for example, is introduced into second solid electrolyte body 12. An electrode 14 having an electrode lead 15 is arranged between first solid electrolyte body 11 and second solid electrolyte body 12 or gas space 13.

The location of gas space 13 beneath electrode 14 and electrode lead 15 is shown with a dotted line in FIG. 1. The electrode has a first layer 21 facing first solid electrolyte body 11 and a second layer 22 facing second solid electrolyte body 12 or gas space 13.

First layer 21 of electrode 14 facing first solid electrolyte body 11 is made of 20 to 60 vol %, preferably 40 vol % $ZrO_2$ stabilized with $Y_2O_3$ and 40 to 80 vol %, preferably 60 vol % platinum. Second layer 22 of electrode 14 facing gas space 13 is made of platinum and has been made porous by adding a pore-forming substance in an amount of 4 to 20 vol %, preferably 10 vol %.

Electrode lead 15 is made of the same material as second layer 22 of electrode 14 and can therefore be applied in a pressure step together with second layer 22.

Another embodiment of the present invention, which is not shown in detail here, is also conceivable, where electrode lead 15 has two layers in at least some areas, the composition of a first layer of electrode lead 15 corresponding to the composition of first layer 21 of electrode 14, and the composition of a second layer of electrode lead 15 corresponding to the composition of second layer 22 of electrode 14.

Figure 3:
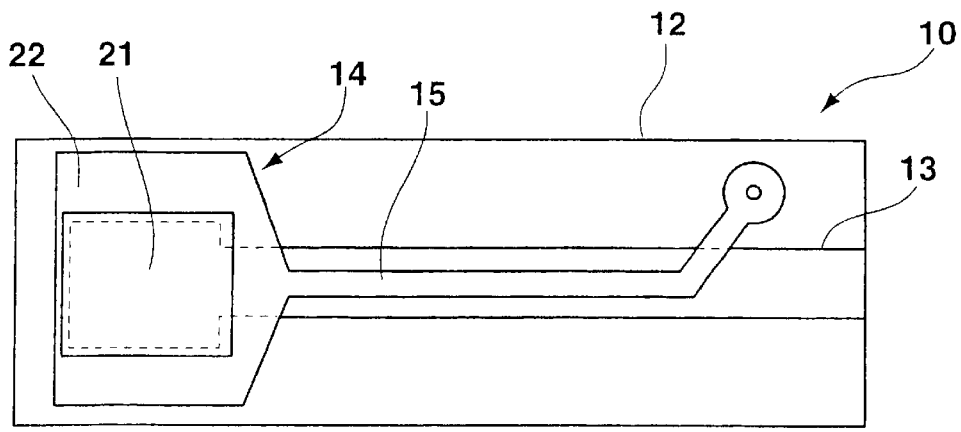
FIG. 3 shows a top view of a large area of a sensor element according to a second embodiment of the present invention.

FIG. 3 shows a top view of a second embodiment of the present invention, omitting first solid electrolyte body 11. Since the first embodiment illustrated in FIG. 1 and the second embodiment illustrated in FIG. 3 differ only in the extent of second layer 22 of electrode 14, the same reference notation has been used for the same elements. In contrast with the first embodiment of the present invention, second layer 22 of electrode 14 in the second embodiment is designed to be significantly wider perpendicular to the longitudinal direction of the sensor element than gas space 13, and it extends almost to the edge of the large area of second solid electrolyte body 12.

In another embodiment of the present invention, first layer 21 of electrode 14 also contains 4 to 12 mol %, preferably 8 mol % $Yb_2O_3$ and/or 0.5 to 2 mol %, preferably 1 mol % $TiO_2$ and/or second layer 22 of electrode 14 also contains 1 to 10 vol %, preferably 5 vol % $Al_2O_3$.

Another embodiment of the present invention is also conceivable, where electrode 14 is arranged on the outer surface of sensor element 10, and gas space 13 is the space surrounding sensor element 10 in the area of this outer surface.

In addition, another embodiment of the present invention is also conceivable, where the electron conductivity of electrode 14 varies continuously between first layer 21 and second layer 22.

If second layer 22 of electrode 14 is arranged so that it covers first layer 21 completely or at least almost completely with respect to gas space 13, then second layer 22 must be porous so that the gas can pass from gas space 13 to first layer 21 of electrode 14.

Furthermore, another embodiment of the present invention, which is not shown in detail here, is also conceivable, where second layer 22 is arranged only in some areas, e.g., in stripes, on first layer 21, so that first layer 21 is in direct contact with gas space 13 in the areas between the stripes. In this case, second layer 22 need not be porous.

What is claimed is:

1. An electrochemical sensor for determining at least one of a gas component and a gas concentration in a gas mixture, comprising:
   an ion-conducting solid electrolyte body; and
   a sensor element including at least one electrode arranged on the solid electrolyte body and exposed to a gas in at least some areas, wherein:
   the at least one electrode includes a first layer facing the solid electrolyte body and a second layer facing the gas,
   the second layer has a higher electron conductivity; and wherein the at least one electrode includes a ceramic component and a metallic component, and a first amount of the ceramic component and the metallic component in the first layer is different than a second amount of the ceramic component and the metallic component in the second layer, the metallic component of the at least one of the first layer and the second layer includes platinum, and the ceramic component of at least one of the first layer and the second layer includes $ZrO_2$ stabilized with $Y_2O_3$ and
   wherein the electrode is connected via an electrode supply lead to a circuit located outside the sensor, the electrode and the electrode supply lead arranged in a gas space formed by the electrolyte body.

2. The sensor according to claim 1, wherein:
   the second layer is porous.

3. The sensor according to claim 1, wherein:
   a porosity of the second layer is greater than a porosity of the first layer.

4. The sensor according to claim 1, wherein:
   the first layer includes 20 to 60 vol % $ZrO_2$ stabilized with $Y_2O_3$ and 40 to 80 vol % platinum.

5. The sensor according to claim 4, wherein:
   the first layer includes at least one of $Yb_2O_3$, $In_2O_3$, and $TiO_2$.

6. The sensor according to claim 5, wherein:
   the first layer includes 0.5 to 2 mol % $TiO_2$.

7. The sensor according to claim 5, wherein:
   the first layer includes 1 mol % $TiO_2$.

8. The sensor according to claim 1, wherein:
   the first layer includes 40 vol % $ZrO_2$ stabilized with $Y_2O_3$ and 60 vol % platinum.

9. The sensor according to claim 1, wherein:
   the second layer includes platinum having a porosity of 4 to 20 vol % due to addition of a pore-forming agent.

10. The sensor according to claim 9, wherein:
    the second layer includes 1 to 10 vol % $Al_2O_3$.

11. The sensor according to claim 9, wherein:
    the second layer includes 5 vol % $Al_2O_3$.

12. The sensor according to claim 1, wherein:
    the second layer includes platinum having a porosity of 10 vol % due to addition of a pore-forming agent.

13. The sensor according to claim 1, further comprising:
    an electrode lead leading to the at least one electrode.

14. The sensor according to claim 13, wherein:
    the electrode lead is made of a material that is the same as that of the second layer.

15. The sensor according to claim 1, wherein:
    the electron conductivity varies continuously within the at least one electrode.

16. An electrochemical sensor for determining at least one of a gas component and a gas concentration in a gas mixture, comprising:
    an ion-conducting solid electrolyte body; and
    a sensor element including at least one electrode arranged on the solid electrolyte body and exposed to a gas in at least some areas, wherein:
    the at least one electrode includes a first layer facing the solid electrolyte body and a second layer facing the gas, and the second layer has a higher electron conductivity than the first layer; wherein the first layer includes 20 to 60 vol % $ZrO_2$ stabilized with $Y_2O_3$ and 40 to 80 vol % platinum wherein the first layer includes at least one of $Yb_2O_3$, $In_2O_3$ and $TiO_2$; and wherein the first layer includes 4 to 12 mol % $Yb_2O_3$.

17. An electrochemical sensor for determining at least one of a gas component and a gas concentration in a gas mixture, comprising:

an ion-conducting solid electrolyte body; and a sensor element including at least one electrode arranged on the solid electrolyte body and exposed to a gas in at least some areas, wherein:

the at least one electrode includes a first layer facing the solid electrolyte body and a second layer facing the gas, and the second layer has a higher electron conductivity than the first layer; wherein the first layer includes 20 to 60 vol % $ZrO_2$ stabilized with $Y_2O_3$ and 40 to 80 vol % platinum wherein the first layer includes at least one of $Yb_2O_3$, $In_2O_3$ and $TiO_2$; wherein the first layer includes 8 mol % $Yb_2O_3$.

18. An electrochemical sensor for determining at least one of a gas component and a gas concentration in a gas mixture, comprising:

an ion-conducting solid electrolyte body; and a sensor element including at least one electrode arranged on the solid electrolyte body and exposed to a gas in at least some areas, wherein:

the at least one electrode includes a first layer facing the solid electrolyte body and a second layer facing the gas, and the second layer has a higher electron conductivity; and wherein the at least one electrode includes a ceramic component and a metallic component, and a first amount of the ceramic component and the metallic component in the first layer is different than a second amount of the ceramic component and the metallic component in the second layer, the metallic component of the at least one of the first layer and the second layer includes platinum, and the ceramic component of at least one of the first layer and the second layer includes $ZrO_2$ stabilized with $Y_2O_3$; and an electrode lead leading to the at least one electrode;

wherein:

the electrode lead includes at least a first layer and a second layer, a composition of the first layer of the electrode lead corresponds to that of the first layer of the at least one electrode, and a composition of the second layer of the electrode lead corresponds to that of the second layer of the at least one electrode.

19. An electrochemical sensor for determining at least one of a gas component and a gas concentration in a gas mixture, comprising:

an ion-conducting solid electrolyte body; and a sensor element including at least one electrode arranged on the solid electrolyte body and exposed to a gas in at least some areas, wherein:

the at least one electrode includes a first layer facing the solid electrolyte body and a second layer facing the gas, and the second layer has a higher electron conductivity; and wherein the at least one electrode includes a ceramic component and a metallic component, and a first amount of the ceramic component and the metallic component in the first layer is different than a second amount of the ceramic component and the metallic component in the second layer, the metallic component of the at least one of the first layer and the second layer includes platinum, and the ceramic component of at least one of the first layer and the second layer includes $ZrO_2$ stabilized with $Y_2O_3$, wherein:

a gas space is introduced into another solid electrolyte body, and the second layer is wider than the gas space at least across a longitudinal extent of the sensor element so that the second layer extends beyond the gas space laterally into an area between the solid electrolyte body and the other solid electrolyte body.

20. An electrochemical sensor for determining at least one of a gas component and a gas concentration in a gas mixture, comprising:

an ion-conducting solid electrolyte body; and a sensor element including at least one electrode arranged on the solid electrolyte body and exposed to a gas in at least some areas, wherein:

the at least one electrode includes a first layer facing the solid electrolyte body and a second layer facing the gas, and the second layer has a higher electron conductivity; and wherein the at least one electrode includes a ceramic component and a metallic component, and a first amount of the ceramic component and the metallic component in the first layer is different than a second amount of the ceramic component and the metallic component in the second layer, the metallic component of the at least one of the first layer and the second layer includes platinum, and the ceramic component of at least one of the first layer and the second layer includes $ZrO_2$ stabilized with $Y_2O_3$; and a gas space arranged in another solid electrolyte body; wherein the second layer covers only some areas of the first layer with respect to the gas space.

* * * * *